United States Patent [19]

Henneberg

[11] 3,996,113
[45] Dec. 7, 1976

[54] EXTRACTIVE DISTILLATION WITH FURFURAL AND ALICYCLIC KETONE SOLVENT

[75] Inventor: Val G. Henneberg, Houston, Tex.

[73] Assignee: Petro-Tex Chemical Corporation, Houston, Tex.

[22] Filed: Mar. 3, 1975

[21] Appl. No.: 554,505

Related U.S. Application Data

[62] Division of Ser. No. 387,920, Aug. 13, 1973, Pat. No. 3,890,208.

[52] U.S. Cl. .................................. 203/58; 203/62; 252/364; 260/681.5 R; 260/677 A
[51] Int. Cl.$^2$ .......................................... B01D 3/40
[58] Field of Search ................. 203/51, 54, 58, 62; 260/681.5, 677 A, 676 R; 252/170, 364; 106/311

[56] References Cited

UNITED STATES PATENTS

| | | | |
|---|---|---|---|
| 2,366,360 | 1/1945 | Semon | 203/54 |
| 2,434,796 | 1/1948 | Hachmuth | 203/54 |
| 2,440,442 | 4/1948 | Hillyer et al. | 252/364 |
| 3,350,282 | 10/1967 | Davis et al. | 203/54 |
| 3,350,283 | 10/1967 | Makin et al. | 203/54 |
| 3,496,069 | 2/1970 | Tschopp et al. | 203/54 |
| 3,546,108 | 12/1970 | Skarada | 252/364 |

*Primary Examiner*—Norman Yudkoff
*Assistant Examiner*—Dale Lovercheck
*Attorney, Agent, or Firm*—N. Elton Dry; Kenneth H. Johnson

[57] ABSTRACT

An extractive distillation cosolvent comprising furfural-alicyclic or acyclic $C_5$–$C_8$ ketone having a boiling point of 130°–180° C., for example cyclohexanone, gives 20% or more improved hydrocarbon solubility and provides a more efficient process for separation of $C_4$ and $C_5$ hydrocarbons of varying degrees of saturation.

10 Claims, No Drawings

EXTRACTIVE DISTILLATION WITH FURFURAL AND ALICYCLIC KETONE SOLVENT

This application is a division of Ser. No. 387,920, filed Aug. 13, 1973 and now U.S. Pat. No. 3,890,208.

BACKGROUND OF THE INVENTION

This invention relates to the separation of organic compounds having closely related boiling points which as a result are difficult to separate. More particularly it relates to an established process for separating such close boiling compounds, i.e., extractive distillation. Even more particularly the invention relates to furfural extractive distillations.

Basically extractive distillation involves distilling the mixture to be separated in the presence of a relatively higher boiling solvent which is selective for a component of the mixture. Extractive distillations are in general performed by causing the solvent to flow down the distillation column as the distillation proceeds, and as vapors ascend from the kettle at the bottom of the column. Thus the vapors are scrubbed by the solvent in a first zone, which selectively dissolves the more soluble component and the resulting fat solvent is partially stripped in a second zone by vapor coming from the distillation kettle and having a higher temperature than the vapor in the first zone. As in ordinary distillation a portion of the overhead product is returned to the distillation column after condensation as reflux, the reflux inlet being positioned several plates above the solvent feed entry. The component dissolved by the solvent may be removed from the solvent by distillation or any other suitable means in order to produce a lean solvent which may be recycled to the extractive distillation.

Extractive distillation is used extensively in the commercial separation of hydrocarbons having 4 to 5 carbons, more particularly the analogues of a particular class of hydrocarbons in this range. For example, $C_4$ hydrocarbon analogues comprising one or more of butadiene, butenes and butanes. The more unsaturated compound in the mixture is more soluble in the solvent, hence the solvent is selective for the more unsaturated compound of the mixture being separated. Thus in the example given, the normal extractive distillation selectively removes butadiene from the vapors having a mixture of butadiene, butenes and butanes. In a similar manner the $C_5$ hydrocarbons are selectively separated. The same selective solubility relationship applies between the butenes and butane if these are the components of the mixture with the butenes being selectively dissolved in the solvent.

The sources of the $C_4$–$C_5$ hydrocarbons are quite diverse such as oxidative dehydrogenation, catalytic or thermal cracking, Fisher-Tropsch reactions and other sources well known to the art. Generally in addition to the hydrocarbons, there are other condensable and non-condensable gases in the feed streams. Thus, the extractive distillation is usually one portion or segment of an overall refining operation which is directed to obtaining one or more of the hydrocarbon components of the feed as product.

There are a number of variations in process equipment and solvent systems proposed in the art and in existence. Foremost among the solvents disclosed in the art and employed in commercial operations is furfural. Furfural may be so prevalent because of its availability and low cost as well as its excellent absorptive separative properties. In any event a large number of existing operations are designed and operated for furfural solvents, similarly a vast amount of technical information has been accumulated in regard to furfural systems. The principal effort of the art in regard to furfural solvent systems has been to improve the efficiency of the system by modification of the manner of operation and not a great deal of success has been achieved in modifying the solvent system to improve the operation of the system. One widely recognized modification of furfural is the addition of minor amounts of polar, lower boiling materials to the furfural, such as water, methanol, ethanol, propanol, acetaldehyde, acetone, methyl ethyl ketone, ether, propyl ether, ethylene dichloride, ethyl acetate, methyl formate, and the like. Water and similar materials are not cosolvents and serve other purposes in the process, principally in regard to providing lower temperatures for stripping solublized hydrocarbon out of the furfural and improving the preferential selectivity of furfural.

A particular problem encountered in adding cosolvents or non-solvents to the furfural system is a possible detriment to solvent selectivity and capacity. It has been found that the addition of most materials, even other solvents to the furfural acts in the same manner as the solvation of hydrocarbon therein, hence reducing the solvent capacity of the furfural.

Another problem relating to the use of cosolvents is the potential for reaction between furfural and the proposed cosolvent. For example, U.S. Pat. No. 2,366,360 to Semon, discloses a number of selective solvents for butadiene such as nitrobutane, nitrobenzene, aniline, dichlorodiethyl ether, ethylene chlorhydrin, dioxane, crotonaldehyde, alpha-ethyl hexanol, cyclohexanone, acetaphenone, mesityl oxide, diethyl oxalate and the like which may be substituted for furfural. The unknowing may misinterpret this teaching to mean that these materials may be partially substituted for furfural. To so misinterpret Semon's teaching can be hazardous. The first substitute disclosed by Semon, i.e., nitrobutane, reacts with carbonyl compounds, such as furfural, to yield unstable nitro alcohols, H. B. Has and E. F. Riley, Chem. Rev. 32, 373 – 430 (1943). The second member of Semon's list, nitrobenzene exhibits similar properties. The third member of the Semon listing, aniline is also reactive with furfural, at room temperatures to yield anils (Schiffs bases).

It is an object of this invention to provide a furfural cosolvent system for extractive distillation which is more efficient than the corresponding furfural system. Another object is to provide a furfural-cosolvent system with no diminution of selectivity for the more unsaturated hydrocarbon than the corresponding furfural system. Another object is to provide a furfural-cosolvent system which can be operable in present furfural equipment. An additional object is to provide a furfural-cosolvent system which will tolerate water in about the same proportions as furfural alone. These and other objects and advantages of the present invention will be apparent from the following discussion.

SUMMARY OF THE INVENTION

Briefly stated the present invention is an improvement in an extractive distillation to separate mixtures of $C_4$ to $C_5$ hydrocarbons of like carbon number and different degrees of saturation including the steps of introducing a selective solvent to an extractive distillation column, introducing said hydrocarbon mixture to be extractively distilled at a point below the point of introduction of said selective solvent, selectively extracting unsaturated hydrocarbon to form a liquid solvent fraction rich in the more unsaturated hydrocarbon, withdrawing a vaporous hydrocarbon fraction as overhead from the top of said extractive distillation column, and withdrawing the solvent rich in the more unsaturated hydrocarbon from the bottom of said distillation column, wherein the improvement is a solvent comprising furfural and from about 1 to 12 weight percent of an acyclic or alicyclic ketone having from 5 to 8 carbon atoms and a boiling point in the range of about 130° to 180° C.

DETAILED DESCRIPTION OF THE INVENTION

The ketone is a cosolvent unlike the polar materials often employed in the prior art. The addition of the particular ketones increased the capacity of the solvent for hydrocarbons and also is not detrimental to the selectivity of the solvent for the more unsaturated hydrocarbons. The ketones are $C_5$ to $C_8$ acyclic and alicyclic ketones having a boiling point in the range of 130°–180° C. or more preferably 140°–170° C. The boiling point of the ketone is an important factor to consider in selecting the ketone. Since the ketone is a cosolvent with the furfural it should perform physically in much the same manner as the furfural which has a boiling point of 161.7° C. The low boiling ketones may tend to volatize out of the solvent mixture under normal operating conditions and hence the benefit would be lost. Ketones boiling above about 180° C. would make the removal or stripping of the extracted hydrocarbon from the fat solvent more difficult, usually requiring higher stripping temperatures and possibly resulting in loss of furfural overhead with the hydrocarbon in the stripper.

Preferably at least about 3% by weight of the ketone and preferably up to about 10% by weight based on dry solvent is employed as cosolvent. The furfural comprises the principal amount of the solvent and will generally comprise from 88 to 99 weight percent of the dry solvent.

Some suitable $C_5$–$C_8$ ketones are (1) alicyclic: cyclopentanone, 2-methyl cyclopentanone, 3-methyl cyclopentanone, or cyclohexanone, (2) acyclic: 3-Methyl-2-hexanone, 4-methyl-2-hexanone, 4-methyl-3-hexanone, 5-methyl-3-hexanone, 2-heptanone, 3-heptanone, 4-heptanone, 3-ethyl-4-methyl-2-pentanone, 3,3-dimethyl-2-hexanone, 3,4-dimethyl-2-hexanone, 2,2-dimethyl-3-hexanone, 2,5-dimethyl-3-hexanone, 4,4-dimethyl-3-hexanone, 2-methyl-4-heptanone, 3-octanone or 4-octanone. Although this listing is not exclusive, it is extensive and discloses most of the ketones suitable in the broadest embodiment of the present invention. Mixtures of various suitable ketones may be employed as well as single combinations with the furfural to provide the benefits of the present invention. A preferred group of ketones would be those having 6 to 7 carbon atoms. Two preferred ketones are cyclohexanone and 2-heptanone.

Very frequently water is present in furfural extractive distillation, as a result of process existencies, for example, resulting in an oxidative dehydrogenation process for preparing the $C_4$ and $C_5$ hydrocarbon feed. Furfural will tolerate water, although it can be detrimental to the extractive portion of the extractive distillation. Generally water in small quantities is considered beneficial for improving the preferential selectivity of the furfural for unsaturated compounds. The presence of the $C_5$–$C_8$ ketones increases the ability of the furfural to tolerate water before there is a knock out of the hydrocarbons. This is a benefit in commercial processes where the water is frequently present in the furfural at a point close to its saturation point. Hence the efficiency of the operation is less likely to be reduced when and if an inadvertent increase in the water should occur.

Generally the present process should operate with no more than 4% by weight of water based on the total of solvent and water in extractive distillation, although up to 7% by weight of water can be present without seriously reducing the efficiency of the system. Generally no more than 10% by weight of water should be present in the extractive distillation, although it may be operable with from 1 up to 25 weight percent water present.

The extractive distillation zone employed may be any type of column or units known to those skilled in the art to be useful in extractive distillations processes. Such columns may include trays or packing and the like. The size of the column, of course, will depend upon the flow rates required and the degree of extraction desired or required. Temperature and pressure are related and are generally matters of choice, often based on the availability of or capacity of cooling and compressing facilities and the like.

The present process is carried out as in any of the prior extractive distillations which generally require feeding a hydrocarbon mixture to be separated to a column at a point below the solvent feed, maintaining temperature and pressure conditions, such that the solvent is in substantially liquid phase and hydrocarbon feed in vapor phase, contacting the vapor phase with the liquid phase, extracting the more unsaturated hydrocarbon into the liquid phase solvent, taking off an overhead that contains a predominant amount of the more saturated hydrocarbon and taking off a bottom that is the fat solvent with the more unsaturated hydrocarbon. There can be various arrangements of refluxes for part of the overhead, premixings of refluxes into solvent, reboilers for the bottom, and stripping columns to separate the solvent and the solubilized hydrocarbon, all of which are conventional techniques for operating a furfural extractive distillation. These and various other process manipulations may be employed in carrying out the present invention.

In practicing the present invention according to its preferred mode of practice, the feed mixture is introduced into the fractionating column at a point approximate to or below the mid-point of the column while the solvent is introduced at a point above the entry point of the feed mixture. The solvent most often is introduced into the extractive distillation column at a point at or near the top of the column. Generally, it will be preferred that the feed mixture be introduced at a point in the fractionating column of from 1/5 to 3/5 the height of the column from the bottom of the column and that the solvent be introduced at a point no greater than ⅓ of the height of the column from the top of the column.

The quantity of solvent required in the present extractive distillation process in order to accomplish the desired separation will vary over relatively wide limits depending upon the efficiency of the separation desired and the equipment used. Generally, no less than one part by volume of solvent per part by volume of feed mixture will be used. The quantity of solvent may range as high as 10 to 40 volumes of solvent per volume of feed mixture. A preferred solvent to feed volume ratio is one within the range of 4:1 to 20:1.

The reflux ratio in which the column is operated will vary according to the theoretical plate efficiency of the column, the solvent to feed ratio, composition of the feed mixture and the separation desired. Generally, however, reflux ratios of 0.01:1 to 20:1 will suffice. It is preferred, however, that the reflux ratio be within the range of 0.5:1 to 5:1.

The present extractive distillation process may be carried out at atmospheric pressure or at super-atmospheric pressures as well as at sub-atmospheric pressures. Generally, pressures within the range of from atmospheric to 200 p.s.i.g. will be used. Preferably, however, the pressure will be within the range of from approximately 40 to 80 p.s.i.g. The temperatures at which the present extractive distillation process may be operated will vary quite widely depending upon the hydrocarbon mixture being separated. Generally, in the usual practice of the present invention, temperatures within the range of 0° to 400° F. will be employed. When the present invention is utilized in accordance with the particularly preferred utility hereinafter defined, temperatures of 100° to 300° F. are commonly employed.

The hydrocarbon separations for which the present invention is particularly suitable include the separation of butadiene from mixtures with butenes and n-butane, the separation of butenes from mixtures with n-butane, the separation of isobutenes from mixtures with isobutane, the separation of pentadiene from pentenes and n-pentane, the separation of pentene from n-pentane, the separation of isopentene from isopentane or other combination wherein a more saturated hydrocarbon is separated from a less saturated hydrocarbon.

The following examples will further describe the invention and its application in extractive distillation, however, the examples are not intended to be the sole scope of the invention or otherwise limit the invention as described hereinabove and recited in the claims.

EXAMPLES 1 – 23

The vapor pressure on a series of runs was measured to determine if the solvents according to the invention solubilized more hydrocarbon than the corresponding furfural solvent. The measurement of vapor pressure is directly proportional to the amount of material in solution, that is, lower vapor pressures at constant temperature and hydrocarbon concentration indicate higher solubility. The composition according to present invention shows 20–25% or more improvement for the solubility of the hydrocarbons. The conditions and results are shown in TABLE I.

The improvement can be viewed directly from TABLE I or the points can be easily plotted for a graphic representation. The improvement in the solubility for hydrocarbons can be determined by a comparison of the mol fraction at a given pressure, which may be done from a graph or the data in TABLE I. For example, Examples 1–4 are a comparison of n-butane solubility in the 100% furfural and 90/10% furfural/cyclohexanone with 1% water. By comparing the same or similar vapor pressures at a particular temperature one can determine the mol fraction. Thus a comparison at 100° F., 100% furfural, pressure of 46 p.s.i.a. (Example 2) represent 0.12 mol fraction hydrocarbon in the solvent and under the same temperature conditions the 90/10% solvent at 47 p.s.i.a. (Example 3) represents 0.15 mol fraction of hydrocarbon in solution. The improvement is 0.03 or about 25% improvement in the hydrocarbon solubility at a given pressure and temperature. This same improvement can be seen in all of the data.

The presence of water can be seen to be a detriment to the efficiency (i.e., hydrocarbon solubility) of both solvents. This reduction of hydrocarbon solubility can further be seen to be greater in regard to 100% furfural and is indicated by the leveling off of the pressure, indicating hydrocarbon saturation, in any particular water percentage series. The detriment is particularly apparent for n-butane in Examples 9–12 where 7% water was present. In other words the 100% furfural — 7% water in Examples 9–12 is saturated at about 0.09 mol fraction of hydrocarbon. It should be noted that Examples 9–12 show that 90/10% solvent — 7% water was not saturated until about 0.12 hydrocarbon mol fraction was solubilized. The mol fraction of hydrocarbon recited in TABLE I is that amount of hydrocarbon in the solvent in question based on the total amount of hydrocarbon and solvent. This figure may be converted to mol percentage by multiplying the mol fraction by 100.

TABLE I

N-Butane Solubility

| | Solvent - 100 Wt.% Furfural Dry Basis | | | | Solvent - 90 Wt.% Furfural Dry Basis 10 Wt.% Cyclohexanone | | | |
|---|---|---|---|---|---|---|---|---|
| | | | Pressure PSIA at | | | | Pressure PSIA at | |
| Example | Wt.% Water | Hydrocarbon Mol Fraction | 100° F | 150° F | Wt.% Water | Hydrocarbon Mol Fraction | 100° F | 150° F |
| 1 | 1.0 | .08 | 35 | 54 | 1.0 | .08 | 32 | 52 |
| 2 | 1.0 | .12 | 46 | 77[1] | 1.0 | .12 | 42 | 68[1] |
| 3 | 1.0 | .15 | 50 | 88 | 1.0 | .15 | 47 | 80 |
| 4 | 1.0 | .22 | 50 | 99 | 1.0 | .22 | 49 | 94 |
| 5 | 4.0 | .07 | 43 | 68 | 4.0 | .07 | 39 | 64 |
| 6 | 4.0 | .10 | 50 | 87 | 4.0 | .10 | 49 | 78 |
| 7 | 4.0 | .13 | 50 | 100 | 4.0 | .13 | 50 | 90 |
| 8 | 4.0 | .20 | 49 | 100[2] | 4.0 | .20 | 50 | 99 |
| 9 | 7.0 | .06 | 45 | 76 | 7.0 | .06 | 38 | 66 |
| 10 | 7.0 | .09 | 50 | 97 | 7.0 | .09 | 48 | 85 |
| 11 | 7.0 | .12 | 49 | 101 | 7.0 | .12 | 49 | 96 |
| 12 | 7.0 | .15 | 51[3] | 102 | 7.0 | .15 | 49 | 100 |
| Butene-1 Solubility | | | | | | | | |
| 13 | 1.0 | .14 | 43 | 73 | 1.0 | .14 | 38 | 65 |
| 14 | 1.0 | .19 | 47 | 82 | 1.0 | .19 | 43 | 76 |
| 15 | 1.0 | .29 | 54 | 98 | 1.0 | .29 | 53 | 94 |

TABLE I-continued

N-Butane Solubility

| | | Solvent - 100 Wt.% Furfural Dry Basis | | | | Solvent - 90 Wt.% Furfural Dry Basis 10 Wt.% Cyclohexanone | | |
|---|---|---|---|---|---|---|---|---|
| | | | Pressure PSIA at | | | | Pressure PSIA at | |
| Example | Wt.% Water | Hydrocarbon Mol Fraction | 100° F | 150° F | Wt.% Water | Hydrocarbon Mol Fraction | 100° F | 150° F |
| 16 | 1.0 | .38 | 58 | 107 | 1.0 | .38 | 56 | 102 |
| 17 | 4.0 | .07 | 30 | 59 | 4.0 | .07 | 28 | 46 |
| 18 | 4.0 | .20 | 55 | 97 | 4.0 | .20 | 50 | 89 |
| 19 | 4.0 | .26 | 57 | 106[4] | 4.0 | .26 | 55[4] | 102 |
| 20 | 7.0 | .06 | 33 | 56 | 7.0 | .06 | 30 | 50 |
| 21 | 7.0 | .13 | 49 | 86 | 7.0 | .13 | 45 | 79 |
| 22 | 7.0 | .19 | 56 | 102 | 7.0 | .19 | 51 | 94 |
| 23 | 7.0 | .22 | 58 | 107 | 7.0 | .25 | 54 | 103 |

[1] mol fraction .11;
[2] mol fraction .19;
[3] mol fraction .16;
[4] mol fraction .27 furfural. The conditions and results of the vapor pressure ratio comparisons are set out in TABLE II.

TABLE II

COSOLVENTS WITH FURFURAL
(Ratios Based on Same $H_2O$ Content)

| | | | 100° F | | 150° F | |
|---|---|---|---|---|---|---|
| Ex. | Solvent Blend Wt.% (Dry Basis) | $H_2O$ Wt.% | $PnC_4$ Furfural $PnC_4$ Solvent | PBu-1 Furfural PBu-1 Solvent | $PnC_4$ Furfural $PnC_4$ Solvent | PBu-1 Furfural PBu-1 Solvent |
| 24 | 100 Furfural | 4 | 1.00 | 1.00 | 1.00 | 1.00 |
|  |  | 7 | 1.00 | 1.00 | 1.00 | 1.00 |
| 25 | 95 Furfural | 4 | 1.01 | 1.04 | 1.05 | 1.04 |
|  | 5 Cyclohexanone | 7 | 1.04 | 1.04 | 1.06 | 1.04 |
| 26 | 90 Furfural | 4 | 1.01 | 1.09 | 1.10 | 1.07 |
|  | 10 Cyclohexanone | 7 | 1.02 | 1.11 | 1.07 | 1.00 |
| 27 | 90 Furfural | 4 | 1.15 | 1.18 | 1.18 | 1.14 |
|  | 10 Heptanone-2 | 7 | 1.10 | 1.20 | 1.24 | 1.18 |
| 28 | 90 Furfural | 4 | 1.00 | 1.03 | 1.08 | 1.05 |
|  | 10 Butyl Cellosolve | 7 | 1.00 | 1.02 | 1.07 | 1.08 |
| 29 | 90 Furfural | 4 | 0.96 | 0.91 | 0.88 | 0.91 |
|  | 10 Sulfolane | 7 | — | — | — | — |
| 30 | 90 Furfural | 4 | 0.95 | 0.97 | 0.98 | 0.98 |
|  | 10 N-methylphr-rolidone | 7 | — | — | — | — |
| 31 | 90 Furfural | 4 | 0.95 | 0.94 | 0.92 | 0.95 |
|  | 10 Butyrolactone | 7 | — | — | — | — |
| 32 | 90 Furfural* | 4 | 1.01 | 1.05 | 1.07 | 1.04 |
|  | 10 Benzaldehyde* | 7 | 1.00 | 1.04 | 1.06 | 1.13 |
| 33 | 90 Furfural | 4 | 0.99 | 0.97 | 1.01 | 0.99 |
|  | 10 MOP | 7 | — | — | — | — |

*Unstable - Precipitate Formed; $PnC_4$ = vapor pressure of n-butane; PBu-1 = vapor pressure of butene-1.

EXAMPLES 24 – 33

In this series of examples the vapor pressure ratio of a number of solvents relative to furfural are presented. These ratios can be compared with that of 100% furfural (Example 24) to indicate whether the solvent is better, the same or worse than furfural alone. Any value above 1.00 indicates better hydrocarbon solubility than furfural, 1.00 indicates the same hydrocarbon solubility as furfural and less than 1.00 indicates poorer hydrocarbon solubility than furfural. The results of the tests on a number of furfural-cosolvent systems are presented in TABLE II. The 90/10% furfural-cyclohexanone (Example 25) shown in Examples 1–23 is compared along with a 95/5% furfural-cyclohexanone system (Example 26). A superior result is also shown for a 90/10% furfural-heptanone-2 solvent according to the present invention.

Surprisingly a number of known $C_4$-$C_5$ hydrocarbon solvents, namely butylcellosolve, sulfolane, n-methylpyrrolidone and 3-methoxyproprionitrile (MOP) were all inferior to furfural alone. It is believed that these compounds acted as hydrocarbons solubilized in the furfural and reduced the solubilizing capacity of the

EXAMPLES 34 – 38

These examples are submitted to show the improvement in the relative volatility of two hydrocarbons of the same number of carbons atoms but varying unsaturation when the solvent according to the present invention is employed. The improvement is shown by the relative vapor pressure of n-butane to butene-1 and butene-1 to butadiene. At constant conditions except for different solvents, the ratio will indicate if there is a change in the relative amount of one of the two materials in the solvent. For example, an increase in the ratio will show that a solvent is preferential for a more unsaturated member of a pair. This is a beneficial change. The volatilities for these examples were determined on 50:50 n-butane: butene-1 blends at varying hydrocarbon concentrations at three temperatures. Similar determinations were made at 130° F for 50:50 blends of butene-1: butadiene. Analysis liquid phase and vapor phase was by Chromatographic area. The amount of water for each run was held constant at 4%. TABLE III shows the conditions and results for the n-butane/butene 1 comparisons. The butene-1/butadiene conditions and results are set in TABLE IV.

TABLE III

| Example | Solvent Blend Wt.% (Dry Basis) | Wt.% Water | Total Hcbn. Mol Fraction | Relative Volatility n-Butane/Butene-1 | | |
|---|---|---|---|---|---|---|
| | | | | 100° F | 130° F | 150° F |
| 34 | 100 Furfural | 4.0 | 0.047 | 1.45 | 1.44 | 1.40 |
| | | | 0.053 | 1.49 | 1.42 | 1.41 |
| | | | 0.073 | 1.44 | 1.41 | 1.39 |
| | | | 0.087 | 1.44 | 1.42 | 1.39 |
| | | | 0.118 | 1.30 | 1.36 | 1.32 |
| | | | 0.129 | 1.43 | 1.39 | 1.36 |
| 35 | 90 Furfural 10 Cyclohexanone | 4.0 | 0.030 | 1.46 | 1.43 | 1.40 |
| | | | 0.031 | 1.47 | 1.43 | 1.40 |
| | | | 0.039 | 1.47 | 1.43 | 1.39 |
| | | | 0.044 | 1.46 | 1.44 | — |
| | | | 0.058 | — | 1.40 | 1.39 |
| | | | 0.078 | 1.37 | 1.28 | 1.38 |
| | | | 0.081 | — | 1.39 | 1.35 |
| | | | 0.083 | 1.39 | 1.28 | 1.38 |
| | | | 0.089 | 1.41 | 1.36 | 1.35 |
| | | | 0.092 | 1.41 | 1.40 | — |
| | | | 0.109 | 1.35 | 1.42 | 1.37 |
| | | | 0.116 | — | 1.36 | 1.34 |
| | | | 0.117 | 1.39 | 1.31 | — |
| | | | 0.122 | 1.34 | 1.34 | 1.32 |
| | | | 0.131 | — | 1.37 | 1.36 |

TABLE IV

| Example | Solvent Blend Wt.% (Dry Basis) | H₂O Wt.% | Total Hydrocarbon Mol Fraction | Relative Volatility Butene-1/ Butadiene |
|---|---|---|---|---|
| 36 | 100 Furfural | 4.0 | 0.044 | 1.78 |
| | | | 0.068 | 1.72 |
| | | | 0.111 | 1.67 |
| | | | 0.139 | 1.64 |
| | | | 0.187 | 1.53 |
| 37 | 90 Furfural 10 Cyclohexanone | 4.0 | 0.023 | 1.76 |
| | | | 0.032 | 1.73 |
| | | | 0.098 | 1.62 |
| | | | 0.110 | 1.56 |
| | | | 0.153 | 1.59 |
| | | | 0.169 | 1.43 |
| 38 | 100 Cyclohexanone | 4.0 | 0.092 | 1.53 |
| | | | 0.105 | 1.53 |
| | | | 0.181 | 1.53 |

EXAMPLE 39

This example demonstrates the result of an attempt to employ aniline as a cosolvent with furfural. Ten drops of aniline were added to 10 cc of furfural. A color change was observed over a 4-minute period from golden to white (precipitate). The white precipitate was a flocculant material. No further tests were made.

The overall results tend to show that the relative volatilities for the 90/10% furfural — cyclohexanone solvent are of the same general degree as furfural alone. This data considered with the improved hydrocarbon solubility demonstrated by the 90/10% furfural — cyclohexanone solvent would provide an extractive distillation in conventional equipment, which at any selected set of conditions will give 20% or greater efficiency to the extraction.

In addition the relative volatility of butene-/butadiene in a 100% cyclohexanone was investigated and found to be substantially inferior to 100% furfural or to the 90/10% furfural-cyclohexanone.

The cyclohexanone alone was not found to be any better as a solvent for hydrocarbons, hence the improvement as a result of its combination in small amounts with furfural was totally unexpected and converse to the action of a number of other cosolvents. (Examples 28–33)

The invention claimed is:

1. In an extractive distillation to separate mixtures of $C_4$ to $C_5$ hydrocarbons selected from the group consisting of saturated and ethylenically unsaturated hydrocarbons of like carbon number and different degrees of saturation including the steps of introducing a selective solvent to an extractive distillation column, introducing said hydrocarbon mixtures to be extractively distilled at a point below the point of introduction of said selective solvent, selectively extracting unsaturated hydrocarbon to form a liquid solvent fraction rich in the more unsaturated hydrocarbon, withdrawing a vaporous hydrocarbon fraction as overhead from the top of said extractive distillation column, and withdrawing the solvent rich in the more unsaturated hydrocarbon from the bottom of said distillation column, wherein the improvement comprises employing as said selective solvent 88 to 99 weight percent furfural and from about 1 to 12 weight percent of an alicyclic ketone having from 5 to 8 carbon atoms and a boiling point in the range of about 130° to 180° C, said weight percent being based on dry solvent.

2. The extractive distillation according to claim 1 where the boiling point range of the ketone is from about 140° to 170° C.

3. The extractive distillation according to claim 2 wherein said ketone has from 6 to 7 carbon atoms.

4. The extractive distillation according to claim 3 wherein said ketone is cyclohexanone.

5. The extractive distillation according to claim 1 wherein said ketone is present in an amount of from about 3 to 10 weight percent.

6. An extractive distillation solvent for separating $C_4$ and $C_5$ hydrocarbons selected from the group consisting of saturated and ethylenically unsaturated hydrocarbons of like carbon number and different degrees of saturation comprising 88–99 weight percent furfural and from 1 to 12 weight percent of an alicyclic ketone having from 5 to 8 carbon atoms having a boiling point in the range of about 130° to 180° C, said weight percents being based on dry solvent.

7. The extractive distillation solvent according to claim 6 wherein said ketone has 6 to 7 carbon atoms and a boiling point in the range of 140° to 170° C.

8. The extractive distillation solvent according to claim 7 wherein said ketone is cyclohexanone.

9. The extractive distillation solvent according to claim 6 containing up to 25 weight percent water.

10. The extractive distillation solvent according to claim 9 containing up to 7 weight percent water.

* * * * *